United States Patent
Liu et al.

(10) Patent No.: US 10,617,734 B2
(45) Date of Patent: Apr. 14, 2020

(54) STAT3 AND ERK SIGNAL PATHWAY INHIBITOR COMPRISING MOGROSIDES AND ANALOGS THEREOF

(71) Applicant: BEIJING UNIVERSITY OF AGRICULTURE, Beijing (CN)

(72) Inventors: Can Liu, Beijing (CN); Lanqing Ma, Beijing (CN); Dequan Dou, Beijing (CN); Yuanxia Sun, Beijing (CN); Long Rong, Beijing (CN); Xiaomeng Zhao, Beijing (CN); Juntao Li, Beijing (CN); Yan Wang, Beijing (CN); Zhengzi Bi, Beijing (CN); Xiaozhu Bi, Beijing (CN); Haiwen Hu, Beijing (CN)

(73) Assignee: BEIJING UNIVERSITY OF AGRICULTURE, Beijing (CN)

( * ) Notice: Subject to any disclaimer, the term of this patent is extended or adjusted under 35 U.S.C. 154(b) by 145 days.

(21) Appl. No.: 15/540,509

(22) PCT Filed: Dec. 23, 2015

(86) PCT No.: PCT/CN2015/098387
§ 371 (c)(1),
(2) Date: Jun. 28, 2017

(87) PCT Pub. No.: WO2016/107471
PCT Pub. Date: Jul. 7, 2016

(65) Prior Publication Data
US 2017/0368130 A1    Dec. 28, 2017

(30) Foreign Application Priority Data
Dec. 30, 2014    (CN) .......................... 2014 1 0841002

(51) Int. Cl.
| | | |
|---|---|---|
| *A61K 36/42* | (2006.01) | |
| *A61K 38/00* | (2006.01) | |
| *C07J 9/00* | (2006.01) | |
| *C07J 17/00* | (2006.01) | |
| *A61K 38/02* | (2006.01) | |
| *A61K 38/17* | (2006.01) | |
| *A61K 39/395* | (2006.01) | |
| *C12Q 1/00* | (2006.01) | |

(52) U.S. Cl.
CPC ............ *A61K 38/005* (2013.01); *A61K 38/02* (2013.01); *A61K 38/1709* (2013.01); *A61K 39/3955* (2013.01); *C07J 9/00* (2013.01); *C07J 17/005* (2013.01); *C12Q 1/00* (2013.01)

(58) Field of Classification Search
None
See application file for complete search history.

(56) References Cited

U.S. PATENT DOCUMENTS

2017/0247735 A1* 8/2017 Houghton-Larsen ........................ C12P 19/18
2018/0346953 A1* 12/2018 Liu .......................... C12P 33/20

FOREIGN PATENT DOCUMENTS

CN    104042620 A  *  9/2014

OTHER PUBLICATIONS

Di, R. et al. Antiinflammatory Activities of Mogrosides from Momordica grosvenori in Murine Macrophages and a Murine Ear Edema Model. J of Agricultural and Food Chemistry 59(3)7474-7481, Jun. 2011. (Year: 2011).*
Notification on the Grant for Patent Right of Invention, dated Feb. 19, 2019, for corresponding priority application CN 201410841002.3 with English translation.

* cited by examiner

*Primary Examiner* — Ralph J Gitomer
(74) *Attorney, Agent, or Firm* — Nath, Goldberg & Meyer; Joshua B. Goldberg; Stephanie Majkut

(57) ABSTRACT

The present invention relates to a chemical and pharmaceutical technology, and in particular to a STAT3 and ERK signal pathway inhibitor and a use thereof. The present invention provides a STAT3 and ERK signal pathway inhibitor. The inhibitor mainly consists of a mogroside and/or an analog thereof. The mogroside and the analog thereof inhibit the phosphorylation of a transcription factor STAT3 and the phosphorylation of an ERK. The method for preparing the mogroside and the analog has the characteristics of simpleness, strong operability and high purity of products. The present invention further provides a use of the STAT3 and ERK signal pathway inhibitor in the preparation of drugs for treating tumors, which realizes the purposes of inhibiting the proliferation of cancer cells and promoting the apoptosis of cancer cells and has a very good inhibition effect on cancers.

7 Claims, 7 Drawing Sheets

STAT3 AND ERK SIGNAL PATHWAY INHIBITOR COMPRISING MOGROSIDES AND ANALOGS THEREOF This is a National Phase Application filed under 35 U.S.C. 371 as a national stage of PCT/CN2015/098387, filed Dec. 23, 2015, an application claiming the benefit of Chinese Application No. 201410841002.3, filed Dec. 30, 2014, the content of each of which is hereby incorporated by reference in its entirety.

TECHNICAL FIELD

The present invention relates to the field of chemical and pharmaceutical technology, and specifically to a STAT3 and ERK signal pathway inhibitor and the use thereof.

BACKGROUND ART

STAT3 is an important member of the family of signal transducers and activators of transcription (STAT), and it is highly expressed in many malignant tissue type tumors and exerts a promoting effect on the tumorigenic progress. STAT3 is activated via phosphorylation after being stimulated by extracellular signals including non-receptor tyrosine kinases, cytokines and growth factors, and forms a phosphorylated STAT3 (P-STAT3). P-STAT3 would be rapidly transferred into cell nucleus and combined with the promoter of a target gene, activating the gene transcription, and further influencing the growth, proliferation and apoptosis of cells. The activation of STAT3 may result in abnormal proliferation and malignant transformation of cells, hence the STAT3 signal pathway is closely related to the occurrence and progression of tumors.

As currently researched, STAT3 is associated with a variety of human tumors, such as colon cancer, pancreatic cancer, lung cancer, lymphoma and so forth. Buettner R. summarized the intervening effect of STAT on tumors and the influence thereof on cell regulation, and discussed the regulation of the STAT signal transduction approach; and Junge WANG discussed a possible mechanism for the regulation of STAT3 signal transduction pathway on G1 to S phase of laryngocarcinoma cells, wherein it was discovered that the STAT3 signal transduction pathway may regulate the transition of G1 to S phase of laryngocarcinoma cells by adjusting the balance between CDK/Cyclin complex and members of cyclin-dependent kinase inhibitors (CKI). With the deep research on STAT3 signal pathway, the role of STAT3 playing in the process of occurrence and progression of tumors draws more and more attention, and a treatment method with STAT3 as the target, which inhibits the activation of STAT3, is expected to open up a novel approach to the treatment of certain malignant tumors.

The activation of STAT3 is achieved via phosphorylation, while the persistent phosphorylation of STAT3 in cells would lead to a series of biological effects, e.g. malignant proliferation and anti-apoptosis of cells. Thus, the use of drugs for inhibiting the phosphorylation of STAT3 is an important breakthrough point in the treatment of cancers.

ERK1/2 is one of the members of mitogen-activated protein kinase (MAPK) superfamily, and participates in a variety of biological reactions such as cell proliferation and differentiation, cell morphology maintenance, cytoskeleton construction, cell apoptosis and malignant transformation of cells; while p-ERK1/2 is a phosphorylated form of ERK1/2, and ERK1/2, after being phosphorylated, enters cell nucleus and acts on transcription factors such as c-myc, c-fos, c-jun, NF-κB, adjusts the transcription of the related genes, and further participates in growth, proliferation and apoptosis of cells. Thus, the activation of this signal transduction pathway is closely related to the occurrence and progression of tumors.

Therefore, the targeted regulation of the STAT3 and ERK signal pathways may be an important approach to the treatment of tumors. The nature world is a huge resource of drugs, and natural products are characterized by novel and various structures and act as an important source for current development of antineoplastic drugs and leading compounds of the drugs.

In view of this, the present invention is specially proposed.

DISCLOSURE OF THE INVENTION

In order to solve the above-mentioned problems in the prior art, the present invention provides a STAT3 and ERK signal pathway inhibitor and the use thereof. In the present invention, high-purity target products, mogrosides and analogs thereof, are prepared through steps of pretreatment, resin separation, hydrolysis, chromatographic purification, etc., wherein the process has the characteristics of simplicity and strong operability, and the purities of the products are greater than 96%. With mogrol serving as a precursor, the mogroside is a triterpenoid produced by glycosylation under the effect of a glycosyltransferase.

By selectively inhibiting the STAT3 and ERK signal pathways, the STAT3 and ERK signal pathway inhibitors provided in the present invention induces the cell cycle arrest of cancer cells and promotes the apoptosis of cancer cells, so as to achieve the efficacy in inhibiting the proliferation of cancer cells. In order to explain the targeted cancer inhibition effect of mogrosides and analogs thereof, Mogroside I E1 monomer and mogroside monomer II A2 monomer are taken as examples in the present invention to depict the targeted cancer inhibition effect of mogroside signal pathway, while mogrol is taken as an example to depict the targeted cancer inhibition effect of the mogrosides and analogs thereof.

In an aspect, the present invention provides a STAT3 and ERK signal pathway inhibitor, wherein the inhibitor mainly consists of mogrosides and/or analogs thereof.

Furthermore, the mogrosides and analogs thereof are able to inhibit phosphorylation of a transcription factor STAT3.

Furthermore, the mogrosides and analogs thereof are able to inhibit phosphorylation of ERK.

The mogrosides and analogs thereof have a pharmacological activity of selectively inhibiting the phosphorylation of ERK, and can achieve the effect of promoting apoptosis of tumor cells by inhibiting the phosphorylation of ERK.

As p-STAT3 and p-ERK1/2 are generally highly expressed in tumor cells, the STAT3 and ERK signal pathway inhibitors provided in the present invention can inhibit tumors, that is, the mogrosides and analogs thereof are targeted intervening agents of p-STAT3 and p-ERK1/2. A variety of tumor cells were selected in the present invention for verification, for example, histiocytic lymphoma cells U937 (lymphoma cells), human melanoma A875 cells (solid tumor cancer cells) and human leukemia K562 cells (leukemia cells K562) were selected to perform intervening experiments of the STAT3 and ERK signal pathways. The results show that the mogrosides and analogs thereof can inhibit the STAT3 and ERK signal pathways and can be applied to inhibiting the proliferation of tumor cells.

Alternatively, the mogrosides and analogs thereof comprise mogrosides, salt derivatives with mogrosides as the parent cores, mogrols and derivatives glycosylated at C3 or C24 position of mogrol or salts thereof. The mogroside may be Mogrol I E1, Mogrol II A2, Mogrol III, Mogrol IV, Mogroside V, or Mogroside VI and so on.

Preferably, the mogrosides are *Momordica grosvenori* mogrosides.

Furthermore, *Momordica grosvenori* mogrosides are prepared through steps of:

1) grinding *Momordica grosvenori*, adding water in accordance with a weight-ratio of 1:6-1:8 between *Momordica grosvenori* and water, performing extraction at a temperature of 80-95° C. for 2-4 times, 1-2 hours each time, and combining extracted solutions;

2) adding chitosan to the combined extracted solutions for flocculation, and removing tannins and soluble proteins from the extracted solutions to provide a clear aqueous solution;

3) utilizing XAD-16 resin for adsorbing the aqueous solution and using 30-50% ethanol for elution to provide a mixed solution of enriched mogrosides in water and ethanol;

4) concentrating the mixed solution under reduced pressure till an extractum status, and recycling the ethanol, and diluting the extractum by adding deionized water of a mass of 4-5 times that of the extractum to the extractum, to provide an aqueous solution of crude mogrosides;

5) performing a decolorization treatment to the aqueous solution of crude mogrosides utilizing Diaion PA resin, and collecting the solution flowing down from the resin column (the solution not absorbed by the resin)

to provide an enriched solution; and 6) concentrating the enriched solution at 50-70° C. under reduced pressure till dry, and adding ethanol for dissolution to obtain a mixture, and then separating the obtained mixture by $C_{18}$ reversed-phase high-performance liquid chromatography with acetonitrile-water as a mobile phase, performing elution in a linear gradient of 20%-75%, collecting target substance, and evaporating solvents to provide white crystalline *Momordica grosvenori* mogrosides with different degrees of glycosylation respectively.

The present invention provides a method for preparing monomers of mogrosides, in this method, high-purity target products are prepared through steps of pretreatment, separation by a particular resin, concentration, separation by a particular resin, concentration, and chromatographic purification, etc., wherein the process has the characteristics of simplicity and strong operability, and the purity of the products are greater than 98%.

Preferably, the analogs of mogrosides are mogrols.

Furthermore, the mogrols are prepared through steps of:

1) grinding *Momordica grosvenori*, adding water in accordance with the weight-ratio of 1:6-1:8 between *Momordica grosvenori* and water, performing extraction at a temperature of 80-95° C. for 2-4 times, 1-2 hours each time, and combining extracted solutions;

2) adding chitosan to the combined extracted solutions for flocculation, and removing tannins and soluble proteins from the extracted solutions to provide a clear aqueous solution;

3) utilizing XAD-16 resin for adsorbing the aqueous solution and using 30-50% ethanol for elution to provide a mixed solution of enriched mogrosides in water and ethanol;

4) concentrating the mixed solution under reduced pressure till an extractum status, and recycling the ethanol, and diluting the extractum by adding deionized water of a mass of 4-5 times that of the extractum to the extractum to provide an aqueous solution of crude mogrosides;

5) performing a decolorization treatment to the aqueous solution of crude glycoside utilizing Diaion PA resin, and collecting the solution flowing down from the resin column to provide an enriched solution;

6) adding a glycosidase to the enriched solution for reaction at a temperature of 45-55° C. for 6-8 hours, wherein the weight of the glycosidase is 4%-6% of the weight of the enriched solution; and 7) performing centrifugation to give a precipitate, wherein the obtained precipitate is a crude product of mogrol, washing the crude product of mogrol with water for 3-5 times to remove water-soluble impurities, and performing freeze drying to provide the mogrol.

In the method for preparing mogrol provided by the present invention, high-purity target products are prepared through steps of pretreatment, separation by a particular resin, hydrolysis, and chromatographic purification, etc., wherein the process has the characteristics of simplicity and strong operability, and the purity of the products are greater than 96%. Mogrol can be obtained after the hydrolysis of glycons of the mogrosides, and mogrols are the precursors for mogroside biosynthesis, while mogrosides are glycosylated derivatives of mogrols. The numbers of glucose groups connected at the positions of C3 and C24 on mogrol backbone are different, hereby forming different mogroside compounds. Mogroside I E1 is a derivative obtained by adding one glycon at C3 position of mogrol; Mogrol II A2 is a derivative obtained by adding two glycons at C3 position of mogrol; and Mogrol III, Mogrol IV, Mogroside V and Mogroside VI and the like can be generated by adding three or more glycons to mogrol, respectively.

In another aspect, the present invention provides the use of the above-mentioned STAT3 and ERK signal pathway inhibitors in the preparation of drugs for treating tumors. The mogrosides and analogs thereof take the STAT3 signal pathway as the drug target; and/or take the ERK signal pathway as the drug target.

The mogrosides and analogs thereof take STAT3 and/or ERK signal pathway as the drug target, which effectively induces the cell cycle arrest of cancer cells and promotes the apoptosis of cancer cells, achieves the objects of inhibiting the proliferation of cancer cells and promoting the apoptosis of cancer cells, and has an excellent inhibitory effect on cancers.

It has been verified that the mogrosides and analogs thereof have a pharmacological activity of selectively inhibiting the activation of the transcription factor STAT3, can inhibit the proliferation of tumor cells and promote their apoptosis, and have an antineoplastic pharmacological activity of inhibiting tumor growth and transfer etc. Western blotting has verified that these compounds exert a significant inhibitory effect on the phosphorylation level of STAT3 (Tyr705), and the inhibitory effect displays a concentration dependence. Furthermore, the mogrosides and analogs thereof take the STAT3 signal pathway as a drug target, and the mogrosides and analogs thereof inhibit the phosphorylation of the transcription factor STAT3.

It has been verified that mogrosides and analogs thereof have a pharmacological activity of selectively inhibiting the activation of the transcription factor STAT3 and regulate the expression of downstream cyclins and apoptotic genes, namely, mogrosides and analogs thereof arrest the cell cycle by up-regulating the cyclin P21 and down-regulating anti-apoptotic protein Bcl-2, so as to achieve the effect of promoting the apoptosis of tumor cells.

Alternatively, the tumors comprise solid tumors and non-solid tumors; wherein the solid tumor is selected from the group consisting of malignant melanoma, prostate cancer, renal carcinoma, head and neck squamous cell carcinoma, lung cancer, ovarian cancer, breast cancer, pancreatic cancer, liver cancer, colon cancer, and other tumors caused by abnormal expression of STAT3 and/or ERK signal pathways;

the non-solid tumor is selected from the group consisting of lymphoma and leukemia; and the leukemia is selected from the group consisting of large granular lymphocytic leukemia, chronic lymphoblastic leukemia and acute lymphoblastic leukemia.

The drugs comprise a drug with mogrosides and analogs thereof as the major active components, or a drug prepared with mogrosides and analogs thereof as the ingredients. The drugs are prepared into inclusion compounds, liposomes, microspheres, nanoparticles or emulsions from the mogrosides and analogs thereof along with pharmaceutically acceptable carriers.

Specifically, the dosage form of the drug may be any one of injection, ampoule, tablet, powder, granule, pill, capsule, suspension and emulsion;

Preferably, the pills include dripping pills and soft pills.

In addition, the mogrosides and analogs thereof in the STAT3 and ERK signal pathway inhibitor provided in the present invention, besides being prepared into drugs, may be also prepared into health care products or foodstuffs, e.g. biscuits, chewing gum, beverages, tea, cream candy, dairy products.

The STAT3 and ERK signal pathway inhibitors and the use thereof provided according to the present invention have at least one of the following beneficial effects:

(1) the use of the STAT3 and ERK signal pathway inhibitors in the preparation of drugs for treating tumors provided in the present invention takes STAT3 and/or ERK signal pathway as the drug target, which effectively induces the cycle arrest of cancer cells and promotes the apoptosis of cancer cells, achieves the objects of inhibiting the proliferation of cancer cells and promoting the apoptosis of cancer cells, and exerts an excellent inhibitory effect on cancers;

(2) the STAT3 and ERK signal pathway inhibitors provided in the present invention are mainly composed of mogrosides and/or analogs thereof, wherein mogrosides and/or analogs thereof have a pharmacological activity of selectively inhibiting the activation of the transcription factor STAT3, regulating the expression of downstream cyclins and apoptotic genes, wherein the mogrosides and analogs thereof arrest the cell cycle by up-regulating the cyclin P21, and simultaneously down-regulate anti-apoptotic protein Bcl-2, so as to achieve the effect of promoting the apoptosis of tumor cells;

(3) the STAT3 and ERK signal pathway inhibitors provided in the present invention further take ERK signal pathway as the drug target, inhibiting the phosphorylation of ERK, and can achieve the effect of promoting the apoptosis of tumor cells by inhibiting the phosphorylation of ERK;

(4) the STAT3 and ERK signal pathway inhibitors provided in the present invention are utilized in the preparation of drugs for treating tumors, wherein the tumors include malignant melanoma, prostate cancer, renal carcinoma, head and neck squamous cell carcinoma, lung cancer, ovarian cancer, breast cancer, pancreatic cancer, liver cancer, colon cancer, lymphoma and leukemia; and (5) the STAT3 and ERK signal pathway inhibitors provided in the present invention are utilized in the preparation of drugs for treating tumors, wherein the drugs are prepared into various dosage forms, and may be prepared into health care products and foodstuffs, so as to achieve the effect of treating tumors.

BRIEF DESCRIPTION OF THE DRAWINGS

In order to more clearly explain the examples of the present invention, the drawings to be used for the examples will be briefly introduced below.

DETAILED DESCRIPTION OF THE EMBODIMENTS

Figure 1:
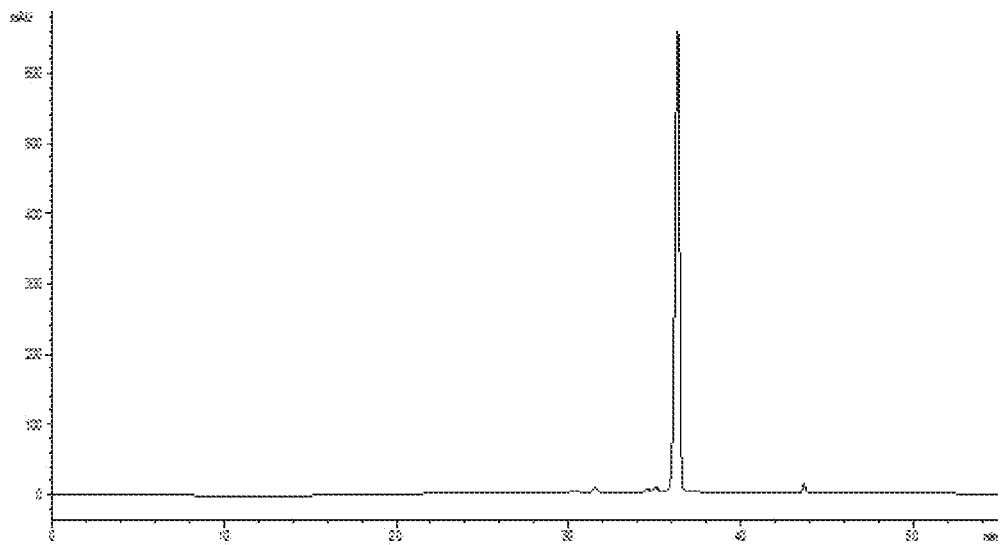
FIG. 1 is an HPLC chromatogram of Mogrol I E1 extracted in Example 1 of the present invention.

In the following contents, the embodiments of the present invention will be described in detail with reference to the examples; however, a person skilled in the art would understand that the following examples are merely used to explain the present invention, rather than being deemed as limiting the scope of the present invention. Examples, for which no concrete situations are specified, are performed according to conventional situations or situations recommended by the manufactures. Reagents or instruments, for which no manufacturers are specified, are conventional products available commercially.

In order to explain the use of the STAT5 and ERK signal pathway inhibitor in the preparation of drugs for treating tumors, the targeted cancer inhibition effect of mogrosides by way of signal pathway is explained by taking Mogrol I E1 and Mogrol II A2 as examples, and the targeted cancer inhibition effect of an analog of mogrosides is explained by taking mogrol as an example.

Example 1

(1) The preparation of Mogroside I E1

Mogroside I E1 was prepared through the steps of:

1) grinding *Momordica grosvenori*, adding water in accordance with a weight-ratio of 1:6 between *Momordica grosvenori* and water, performing extraction at a temperature of 80° C. for twice, 1 hour each time, and combining extracted solutions;

2) adding chitosan to the combined extracted solutions for flocculation, and removing tannins and soluble proteins from the extracted solutions to provide a clear aqueous solution;

3) utilizing XAD-16 resin for adsorbing the aqueous solution and using 30% ethanol for elution to provide a mixed solution of enriched mogrosides in water and ethanol;

4) concentrating the mixed solution under reduced pressure till an extractum status, and recycling the ethanol, and diluting the extractum by adding deionized water of a mass of 4 times that of the extracturn to the extractum, to provide an aqueous solution of crude mogrosides;

5) performing a decolorization treatment to the aqueous solution of crude mogrosides utilizing Diaion PA resin, and collecting the solution flowing down from the resin column to provide an enriched solution; and 6) concentrating the enriched solution at 50° C. under reduced pressure till dry, and adding ethanol for dissolution to obtain a mixture, and then separating the obtained mixture by $C_{18}$ reversed-phase high-performance liquid chromatography with acetonitrile-water as a mobile phase, performing elution in a linear gradient of 20%-75%, collecting target substance, and evaporating solvents to provide Mogroside I E1 as a white crystal.

The molecular formula of the obtained Mogroside I E1 is $C_{36}H_{62}O_9$, with a molecular weight of 638.9 and a CAS Registry Number: 88901-39-7, and the structural formula of Mogroside I E1 is

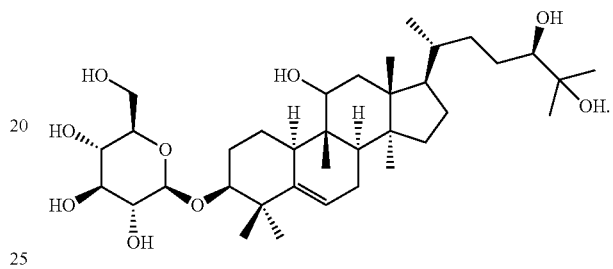

(2) The preparation of Mogroside II A2

Mogroside II A2 was prepared through the steps of:

1) grinding *Mornordica grosvenori*, adding water in accordance with a weight-ratio of 1:8 between *Mornordica grosvenori* and water, performing extraction at 95° C. for 4 times, 2 hours each time, and combining extracted solutions;

2) adding chitosan to the combined extracted solutions for flocculation, and removing tannins and soluble proteins from the extracted solutions to provide a clear aqueous solution;

3) utilizing XAD-16 resin for adsorbing the aqueous solution and using 50% ethanol for elution to provide a mixed solution of enriched mogrosides in water and ethanol;

4) concentrating the mixed solution under reduced pressure till an extractum status, and recycling the ethanol, and diluting the extractum by adding deionized water of a mass of 5 times that of the extractum to the extractum, to provide an aqueous solution of crude mogrosides;

5) performing a decolorization treatment to the aqueous solution of crude mogrosides utilizing Diaion PA resin, and collecting the solution flowing down from the resin column to provide an enriched solution; and concentrating the enriched solution at 50° C. under reduced pressure till dry, and adding ethanol for dissolution to obtain a mixture, and then separating the obtained mixture by $C_{18}$ reversed-phase high-performance liquid chromatography with acetonitrile-water as a mobile phase, performing elution in a linear gradient of 20%-75%, collecting target substance, and evaporating solvents to provide Mogroside II A2 as a white crystal.

The obtained Mogroside II A2 has a CAS Registry Number: 88901-45-5, with a molecular formula of $C_{42}H_{72}O_{14}$ and a molecular weight of 801.01, and the structural formula of Mogroside II A2 is

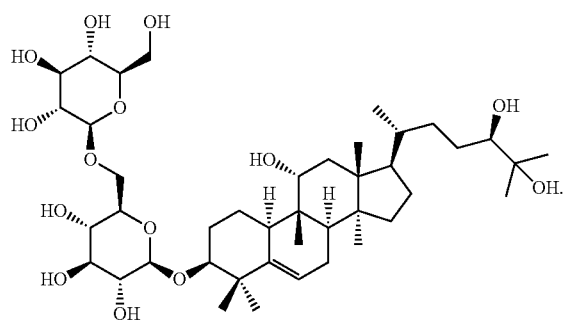

Figure 2:
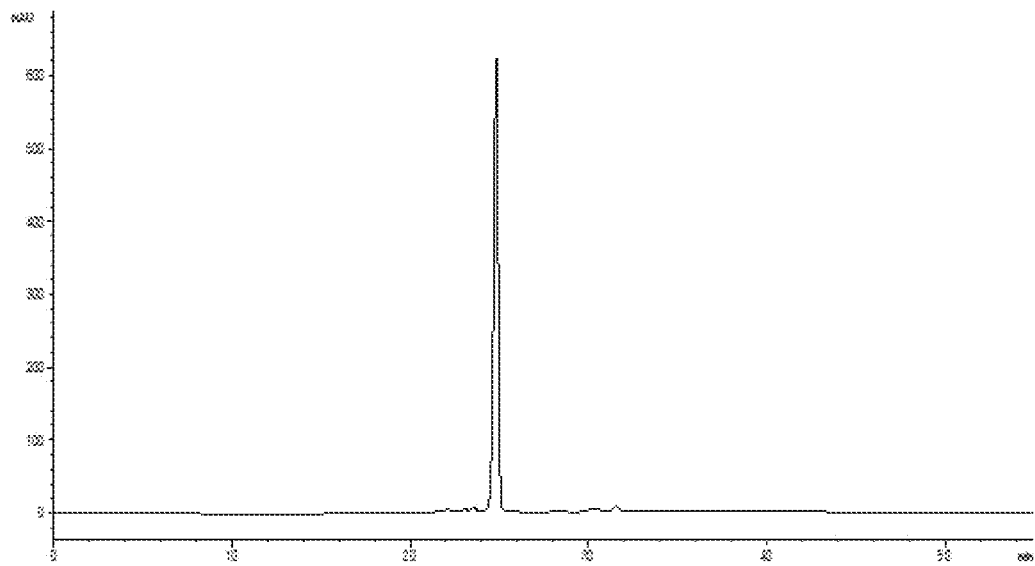
FIG. 2 is an HPLC chromatogram of Mogrol II A2 extracted in Example 1 of the present invention.

Performing the HPLC analysis on the obtained Mogroside I E1 and Mogroside II A2, and the obtained chromatograms are shown in FIGS. 1 and 2. It can be seen from FIGS. 1 and 2 that Mogroside I E1 and Mogroside II A2 prepared through the method for preparing the mogrosides and analogs thereof according to the present invention both have a purity of higher than 96%.

Example 2

The preparation of mogrols:

(1) A method for preparing Mogrol I included the steps of:

1) grinding *Momordica grosvenori*, adding water in accordance with the weight-ratio of 1:6 between *Mornordica grosvenori* and water, performing extraction at a temperature of 80° C. for twice, 1 hour each time, and combining extracted solutions;

2) adding chitosan to the combined extracted solutions for flocculation, and removing tannins and soluble proteins from the extracted solutions to provide a clear aqueous solution;

3) utilizing XAD-16 resin for adsorbing the aqueous solution and using 30% ethanol for elution to provide a mixed solution of enriched mogrosides in water and ethanol;

4) concentrating the mixed solution under reduced pressure till an extractum status, and recycling the ethanol, and diluting the extractum by adding deionized water of a mass of 4 times that of the extractum to the extractum to provide an aqueous solution of crude mogrosides;

5) performing a decolorization treatment to the aqueous solution of crude glycoside utilizing Diaion PA resin, and collecting the solution flowing down from the resin column to provide an enriched solution;

6) adding a glycosidase to the enriched solution for reaction at a temperature of 45° C. for 6 hours, wherein the weight of the glycosidase is 4% of the weight of the enriched solution; and 7) performing centrifugation to give a precipitate, wherein the obtained precipitate is a crude product of mogrol, washing the crude product of mogrol with water for 3 times to remove water-soluble impurities, and performing freeze drying to provide Mogrol I.

The obtained Mogrol I has a molecular weight of 476.7 and a CAS Registry Number: 88930-15-8, the molecular formula thereof is $C_{30}H_{52}O_4$, and the structural formula thereof is

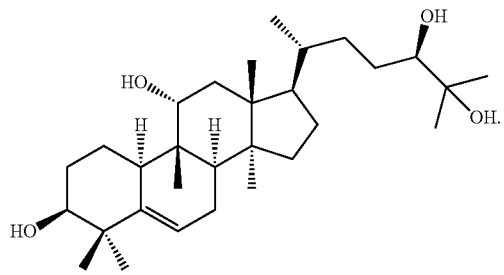

Figure 3:
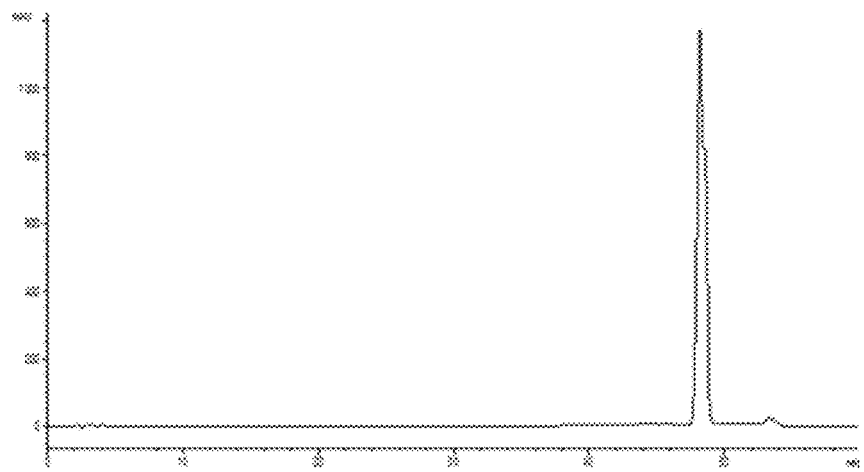
FIG. 3 is an HPLC chromatogram of mogrol extracted in Example 2 of the present invention.

Performing the HPLC analysis to the obtained Mogrol I, and the obtained chromatogram is shown in FIG. 3. It can be seen from FIG. 3 that Mogrol I prepared through the method for preparing mogrol provided in the present invention has a purity of higher than 98%.

(2) A method for preparing Mogrol II included the steps of:

1) grinding *Momordica grosvenori*, adding water in accordance with the weight-ratio of 1:8 between *Momordica grosvenori* and water, performing extraction at a temperature of 95° C. for 4 times, 2 hours each time, and combining extracted solutions;

2) adding chitosan to the combined extracted solutions for flocculation, and removing tannins and soluble proteins from the extracted solutions to provide a clear aqueous solution;

3) utilizing XAD-16 resin for adsorbing the aqueous solution and using 50% ethanol for elution to provide a mixed solution of enriched mogrosides in water and ethanol;

4) concentrating the mixed solution under reduced pressure till an extractum status, and recycling the ethanol, and diluting the extractum by adding deionized water of a mass of 4-5 times that of the extractum to the extractum to provide an aqueous solution of crude mogrosides;

5) performing a decolorization treatment to the aqueous solution of crude glycoside utilizing Diaion PA resin, and collecting the solution flowing down from the resin column to provide an enriched solution;

6) adding a glycosidase to the enriched solution for reaction at a temperature of 55° C. for 8 hours, wherein the weight of the glycosidase is 6% of the weight of the enriched solution; and 7) performing centrifugation to give a precipitate, wherein the obtained precipitate is a crude product of mogrol, washing the crude product of mogrol with water for 5 times to remove water-soluble impurities, and performing freeze drying to provide Mogrol II.

The obtained Mogrol II has a molecular weight of 476.7 and a CAS Registry Number: 88930-15-8, the molecular formula thereof is $C_{30}H_{52}O_4$, and the structural formula thereof is

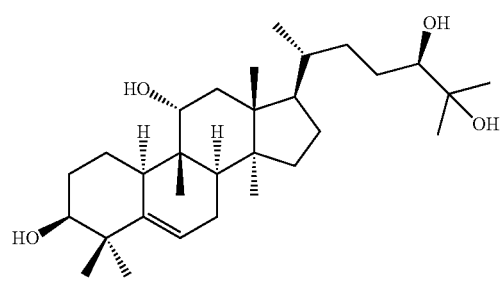

Performing the HPLC analysis on the obtained Mogrol II, and an identical result to that of the above-mentioned Mogrol I was obtained, namely, the purity of the obtained Mogrol II was also higher than 98%. As the structures of the above-mentioned Mogrol I and Mogrol II are identical, Mogrol I and Mogrol II can be both referred to in the present application as mogrol.

Example 3

Figure 4:
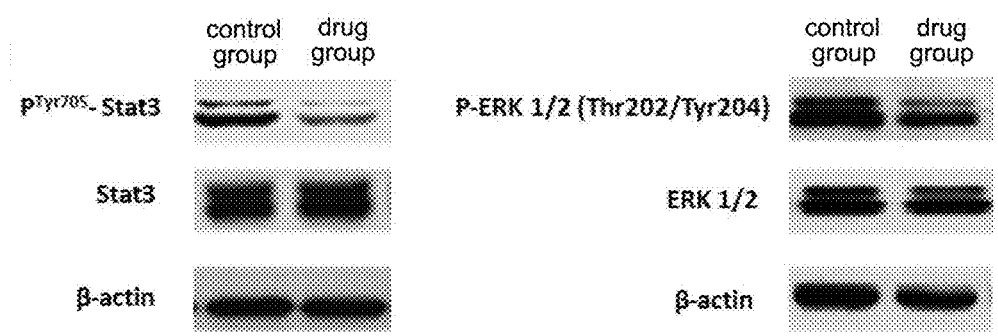
FIG. 4 is a variation diagram for expression levels of phosphorylated ERK1/2 (P-ERK1/2) and phosphorylated STAT3 (P-STAT3) upon the action of Mogrol I E1 on lymphoma U937 cells according to Example 3 of the present invention.
Figure 5:
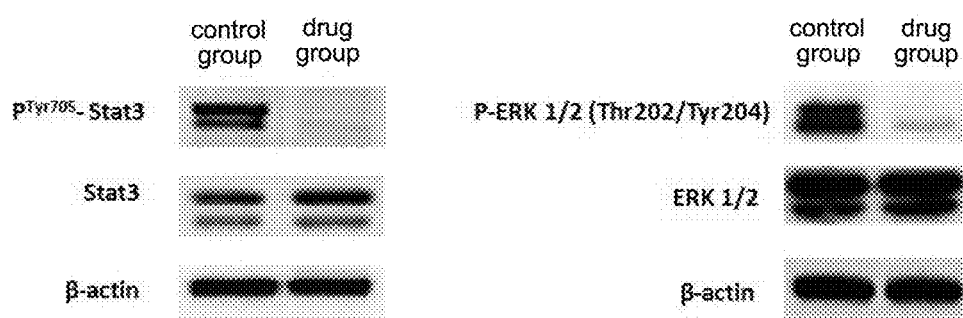
FIG. 5 is a variation diagram for expression levels of phosphorylated ERK1/2 (P-ERK1/2) and phosphorylated STAT3 (P-STAT3) upon the action of Mogrol II A2 on melanoma A875 cells according to Example 3 of the present invention.
Figure 6:
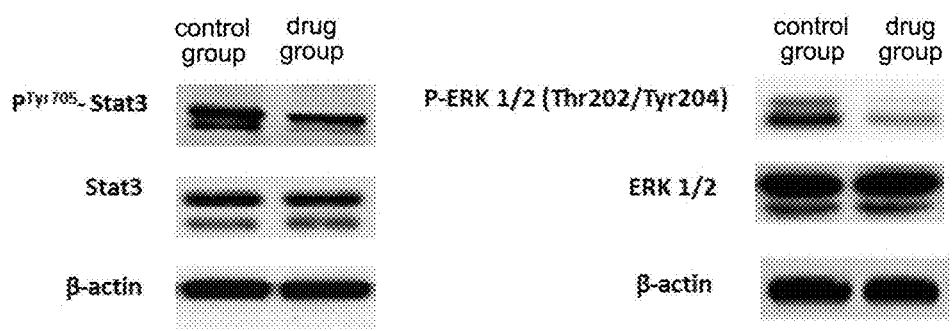
FIG. 6 is a variation diagram for expression levels of phosphorylated ERK1/2 (P-ERK1/2) and phosphorylated STAT3 (P-STAT3) upon the action of Mogrol II A2 on leukemia cells K562 according to Example 3 of the present invention.

The inhibition of the STAT3 and ERK signal pathways achieved by Mogroside I E1, Mogroside II A2 and mogrol was detected by Western Blotting, specifically:

Group 1: histiocytic lymphoma U937 cells ($1 \times 10^6$ cells/well) were inoculated into a 6-well culture plate for staying overnight, and 0 and 10 µmol/L of Mogroside I E1, Mogroside II A2 and mogrol were added respectively, and the culture was continued for 24 hours;

Group 2: human melanoma A875 cells ($1 \times 10^6$ cells/well) were inoculated into a 6-well culture plate for staying overnight, and 0 and 10 µmol/L of Mogroside I E1, Mogroside II A2 and mogrol were added respectively, and the culture was continued for 24 hours;

Group 3: leukemia cells K562 ($1 \times 10^6$ cells/well) were inoculated into a 6-well culture plate for staying overnight, and 0 and 10 µmol/L of Mogroside I E1 Mogroside II A2 and mogrol were added respectively, and the culture was continued for 24 hours;

After the termination of the cell culture, the culture solution was removed, and the residue was washed with PBS (0.01 mol/L, pH 7.4), and then a cell lysis solution containing protease inhibitors was added at an amount of 50 µl/well, and the mixture was placed in an ice bath for lysis at 4° C. for 30 min and then centrifuged at 14000 r/min for 10 min, and then total proteins were obtained from the supernatant;

The protein concentrations were measured with bovine serum albumin (BSA) as the standard. 50 µg of the total proteins was separated by polyacrylamide gel electrophoresis with 12% SOS, electrophoretically transferred to a PVDF membrane (polyvinylidene fluoride membrane), and blocked for 1 h by 5% of skim milk (containing 0.1% of Tween 20), and then antibodies p-STAT3 (Tyr705) and p-Erk1/2 as well as β-actin were added, and the primary antibody was incubated at 4° C. overnight (β-actin was used as reference in loading amount); the membrane was washed for 3 times with TBS-T, 5 min each time; secondary antibody marked by horseradish peroxidase (HRP) was added for incubation at room temperature for 1 h, the membrane was washed for 3 times with a wash solution (TBS-T), 10 min each time, and then ECL was added for incubation in dark for 5 min, and subsequently, a fluorescence imaging analyzer was used for image development and scanning analysis, and the results of Western Blotting detection are shown in FIGS. 4 to 6.

Results obtained after U937 cell treatment by Mogrol I E1, Mogrol II A2 and mogrol were identical to each other. Taking the effect of Mogrol I E1 on U937 cells as an example, details are shown in FIG. 4. It can be seen that the expression levels of phosphorylated ERK1/2 (P-ERK1/2) and phosphorylated STAT3 (P-STAT3) were significantly decreased after the mogrosides and analogs thereof acted on the U937 cells for 24 hours. In addition, 0, 10, 150 and 250 µmol/L of the mogrosides and analogs thereof were used for treating the U937 cells for 24 hours, and the results showed that the decreasing degree of the expression levels of phosphorylated ERK1/2 (P-ERK1/2) and phosphorylated STAT3 (P-STAT3) was enhanced with the increase of the treatment concentration of the mogrosides and analogs thereof. It indicates that mogrosides and analogs thereof have effects of inhibiting the activation of STAT3 and ERK proteins and blocking the STAT3 and ERK signal pathways.

Figure 7:
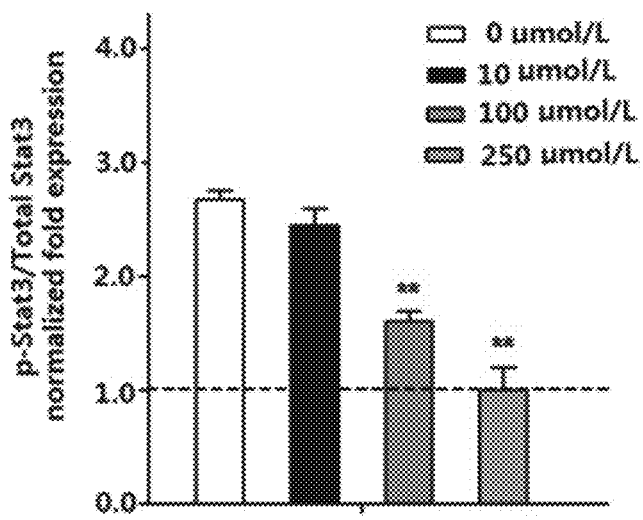
FIG. 7 is a variation diagram for expression levels of phosphorylated STAT3 (P-STAT3) upon the action of the mogrol on melanoma A875 cells and lymphoma U937 cells according to Example 3 of the present invention.
Figure 8:
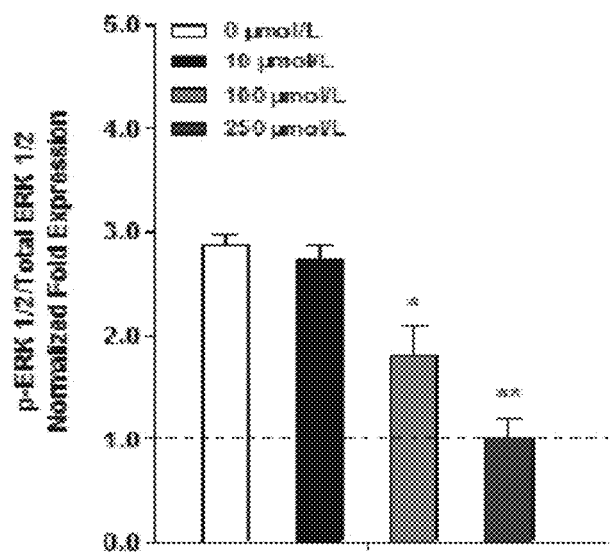
FIG. 8 is a variation diagram for expression levels of phosphorylated ERK1/2 (P-ERK1/2) upon the action of the mogrol on melanoma A875 cells and lymphoma U937 cells according to Example 3 of the present invention.

Results obtained after melanoma A875 cell treatment by Mogrol I E1 Mogrol II A2 and the mogrol were identical to each other. The effect of Mogrol II A2 on melanoma A875 cells is shown in FIG. 5; in addition, the effect of the mogrol on melanoma A875 cells is shown in FIGS. 7 and 8. It can be seen that the expression levels of phosphorylated ERK1/2 (P-ERK1/2) and phosphorylated STAT3 (P-STAT3) were significantly decreased after the mogrosides and analogs thereof acted on the melanoma A875 cells for 24 hours. In addition, it has been verified by experiments that the decreasing degree of the expression levels of phosphorylated ERK1/2 (P-ERK1/2) and phosphorylated STAT3 (P-STAT3) was enhanced with the increase of the treatment concentration of the mogrosides and analogs thereof, which was identical to the results of U937 cells. It indicates that mogrosides and analogs thereof have the effects of inhibiting the activation of STAT3 and ERK proteins and blocking the STAT3 and ERK signal pathways.

Results obtained after leukemia cell K562 treatment by Mogrol I E1, Mogrol II A2 and mogrol were identical to each other. Taking the effect of Mogrol II A2 on leukemia cells K562 as an example, details are shown in FIG. 6. It can be seen that the expression levels of phosphorylated ERK1/2 (P-ERK1/2) and phosphorylated STAT3 (P-STAT3) were significantly decreased after the mogrosides and analogs thereof acted on the leukemia cells K562 for 24 hours. Moreover, it has been verified by experiments that the decreasing degree of the expression levels of phosphorylated ERK1/2 (P-ERK1/2) and phosphorylated STAT3 (P-STAT3) was enhanced with the increase of the treatment concentration of the mogrosides and analogs thereof, which was identical to the results of U937 cells. It indicates that mogrosides and analogs thereof have the effects of inhibiting the activation of STAT3 and ERK proteins and blocking the STAT3 and ERK signal pathways.

Example 4

The STAT3 and ERK signal pathways can regulate cyclins and apoptosis genes, and in order to verify the effects of Mogrol I E1 Mogrol II A2 and mogrol, the expression status of downstream genes of STAT3 and ERK was detected, wherein the influences of the three mogrosides and analogs thereof, i.e. Mogrol I E1, Mogrol II A2 and mogrol, on Bcl-2 and P21 proteins in the histiocytic lymphoma U937 cells, human melanoma A875 cells and leukemia cells K562 were determined, respectively.

The regulation of Bcl-2 and P21 proteins by mogrosides and analog thereof to the was detected by Western Blotting, specifically: histiocytic lymphoma U937 cells, human melanoma A875 cells and leukemia cells K562 ($1 \times 10^6$ cells/well) were inoculated into a 6-well culture plate overnight, and 0 and 10 µmol/L of the mogrosides and analogs thereof were added respectively, and kept cultured for 24 h. After the termination of the cell culture, the culture solution was removed, and the residue was washed with PBS (0.01 mol/L, pH 7.4), then a cell lysis solution containing protease inhibitors was added at an amount of 50 µl/well, and the mixture was placed in an ice bath for lysis at 4° C. for 30 min and then centrifuged at a speed of 14000 r/min for 10 min, and then total proteins were obtained from the supernatant.

Figure 9:
FIG. 9 is a variation diagram of expression levels of cycle regulatory protein P21 and anti-apoptotic protein Bcl-2 upon the action of Mogrol I E1 on lymphoma U937 cells according to Example 4 of the present invention.
Figure 10:
FIG. 10 is a variation diagram of expression levels of cycle regulatory protein P21 and anti-apoptotic protein Bcl-2 upon the action of Mogrol II A2 on melanoma A875 cells according to Example 4 of the present invention.
Figure 11:
FIG. 11 is a variation diagram of expression levels of cycle regulatory protein P21 and anti-apoptotic protein Bcl-2 upon the action of the mogrol on leukemia cells K562 according to Example 4 of the present invention.

The protein concentration was measured with bovine serum albumin (BSA) as the standard. 50 µg of the total proteins were separated by polyacrylamide gel electrophoresis with 12% SDS, and electrophoretically transferred to a PVDF membrane (polyvinylidene fluoride membrane), and blocked for 1 h by 5% of skim milk (containing 0.1% of Tween 20), and then antibodies P21, Bcl-2 and β-actin were added, wherein the primary antibody was incubated at 4° C. overnight (β-actin was used as reference loading amount); the membrane was washed for 3 times with TBS-T, 5 min each time; secondary antibody marked by horseradish peroxidase (HRP) was added for incubation at room temperature for 1 h, the membrane was washed with rinse solution (TBS-T) for 3 times, 10 min each time, and then ECL was added for incubation in dark for 5 min, and subsequently, a fluorescence imaging analyzer was used for image development and scanning analysis. The results of Western Blotting detection are shown in FIGS. 9 to 11.

Results obtained after U937 cell treatment by Mogroside I E1, Mogroside II A2 and mogrol were identical to each other. Taking the effect of Mogroside I E1 on the U937 cells as an example, details are shown in FIG. 9. It can be seen that the downstream cycle regulatory protein P21 associated with the STAT3 signal was significantly up-regulated, while the anti-apoptotic protein Bcl-2 was significantly down-regulated after the mogrosides and analogs thereof acted on the U937 cells for 24 h. In addition, 0, 10, 150 and 250 µmol/L of different mogrosides and analogs thereof were used for treating U937 cells for 24 h. After different concentrations of mogrosides and analogs thereof acted on U937 cells for 24 h, the mogrosides and analogs thereof can all inhibit the activation of STAT3 in a dose-dependent way, and simultaneously up-regulate the cycle regulatory protein P21 and inhibit the expression of the anti-apoptotic protein Bcl-2. The expression levels of P21 and Bcl-2 proteins exhibit a drug-concentration dependence, and it indicates that mogrosides and analogs thereof regulate the expression of the downstream cyclins and apoptosis genes of the signal pathway by blocking the STAT3 and ERK sites, so as to achieve the effects of inhibiting the growth of cancer cells and promoting the apoptosis of cancer cells.

Results obtained after melanoma A875 cell treatment by Mogroside I E1 Mogroside II A2 and mogrol were identical to each other. Taking the effect of Mogroside II A2 on the melanoma A875 cells as an example, details are shown in FIG. 10. It can be seen that the downstream cycle regulatory protein P21 associated with the STAT3 signal was significantly up-regulated, while the anti-apoptotic protein Bcl-2 was significantly down-regulated, after the mogrosides and analogs thereof acted on the human melanoma A875 cells for 24 h. In addition, it is proved by experiments that after different concentrations of mogrosides and analogs thereof acted on the human melanoma A875 cells for 24 h, the mogrosides and analogs thereof can inhibit the activation of STAT3 in a dose-dependent way, and simultaneously up-regulate the cycle regulatory protein P21 and inhibit the expression of the anti-apoptotic protein Bcl-2, and the results are identical to those of the U937 cells. The expression levels of P21 and Bcl-2 proteins exhibit a drug-concentration dependence, and it indicates that the mogrosides and analogs thereof regulate the expression of the downstream cyclins and apoptosis genes of the signal pathway by blocking the STAT3 and ERK sites, so as to achieve the effects of inhibiting the growth of cancer cells and promoting the apoptosis of cancer cells.

Results obtained after leukemia cell K562 treatment by Mogroside I E1 Mogroside II A2 and mogrol were identical to each other. Taking the effect of the mogrol on the leukemia cells K562 as an example, details are shown in FIG. 11. It can be seen that the downstream cycle regulatory protein P21 associated with the STAT3 signal was significantly up-regulated, while the anti-apoptotic protein Bcl-2 was significantly down-regulated, after the mogrosides and analogs thereof acted on the leukemia cells K562 for 24 h; moreover, it is proved by tests that after that different concentrations of mogrosides and analogs thereof acted on the leukemia cells K562 for 24 h, the mogrosides and analogs thereof can inhibit the activation of STAT3 in a dose-dependent way, and simultaneously up-regulate the cycle regulatory protein P21 and inhibit the expression of the anti-apoptotic protein Bcl-2, and the results were identical to those of the U937 cells. The expression levels of the P21 and Bcl-2 proteins exhibit a drug-concentration dependence, and it indicates that mogrosides and analogs thereof regulate the expression of the downstream cyclins and apoptosis genes of the signal pathway by blocking the STAT3 and ERK sites, so as to achieve the effects of inhibiting the growth of cancer cells and promoting the apoptosis of cancer cells.

Bcl-2 is an anti-apoptotic protein and can inhibit programmed cell death, and the overexpression of Bcl-2 is an important cause of malignant cell proliferation, while Bcl-2 is a downstream protein regulated by STAT3. When the phosphorylation of STAT3 proteins in U937 cells, human melanoma A875 cells and leukemia cells K562 treated by the mogrosides and analogs thereof (Mogroside I E1, Mogroside II A2 and mogrol) was inhibited, the expression of Bcl-2 protein was significantly decreased, and the expression level of Bcl-2 protein was positively correlated with the inhibition suffered by STAT3, which is also an important reason for the promotion of apoptosis of cancer cells.

Example 5

The influences of Mogroside I E1, Mogroside II A2 and mogrol on the cell cycle distribution of the histiocytic lymphoma U937 cells, the human melanoma A875 cells and the leukemia cells K562.

The cell cycle arrest achieved by drugs is an important approach to the inhibition of cancer cell proliferation. Histiocytic lymphoma U937 cells, human melanoma A875 cells and leukemia cells K562 in logarithmic growth phase were selected, and after the respective culture with 0 and 10 µmol/L of the mogrosides and analogs thereof (Mogroside I E1, Mogroside II A2 and the mogrol) for 24 h, 0.25% pancreatin was added for digestion, the cells of the drug groups and the control groups were collected and washed with PBS and then centrifuged at 2500 rpm for 5 min, and then the cells were collected, fixed with 70% cold ethanol, and stayed overnight at 4° C., which was then subjected to centrifugation to remove ethanol, and PBS containing RNase A was added, and propidium iodide (PI) was added for staining, and the resulting mixture was mixed evenly (RNase A had a final concentration of 50 mg/L, and the final concentration of PI was 25 mg/L), incubated in dark at 37° C. for 30 min, and detected by flow cytometer.

The STAT3 signal pathway relates to the expression of cell cycle genes, and accordingly influences the cell cycle progression. The results obtained after U937 cell treatment by Mogroside I E1, Mogroside II A2 and mogrol were identical to each other. It can be concluded from the detection results of the flow cytometer that cells of G0/G1 phase of the lymphoma U937 cells have a gradually increasing proportion after the treatment by the mogrosides and analogs thereof, which indicates that mogrosides and analogs thereof can lead to the G0/G1 arrest of the U937 cells.

In addition, 0, 1, 10, 150 and 250 μmol/L of the three mogrosides and analogs thereof were used for treating the U937 cells for 24 h, and the results obtained after U937 cell treatment by Mogroside I E1, Mogroside II A2 and mogrol were identical to each other. It is concluded that with the rise of the concentration of the mogrosides and analogs thereof, the proportion of cells in G0/G1 phase is gradually increased, and the cell cycle distribution is significantly changed, which indicates that mogrosides and analogs thereof can lead to the G0/G1 arrest of the U937 cells, and the cycle arrest effect of the mogrosides and analogs thereof on cancer cells exhibits a dose-dependence. It indicates that mogrosides and analogs thereof can induce the cell cycle arrest of tumor cells by inhibiting the STAT3 signal pathway and regulating cyclins, so as to inhibit the growth of tumors.

Figure 12:
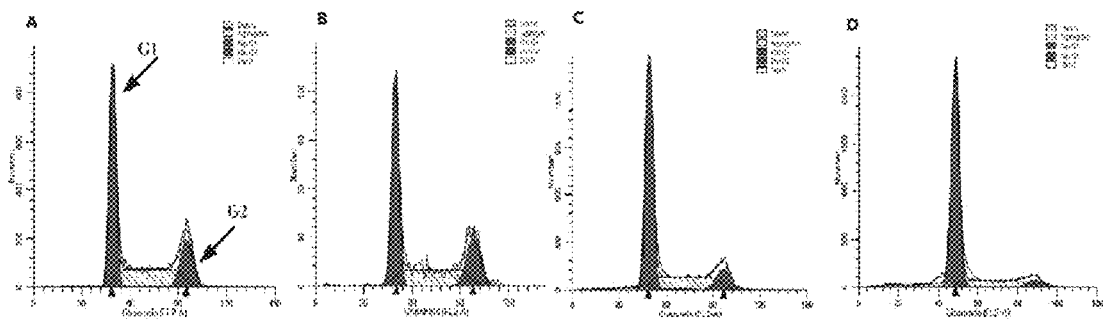
FIG. 12 is a variation diagram of cell cycle upon the action of different concentrations of the mogrol on melanoma A875 cells according to Example 5 of the present invention.

The results obtained after melanoma A875 cell treatment by Mogroside I E1, Mogroside II A2 and mogrol were identical to each other. It can be concluded from the detection results of the flow cytometer that the cells in the G0/G1 phase of human melanoma A875 cells have a gradually increasing proportion after the treatment by mogrosides and analogs thereof, which indicates that mogrosides and analogs thereof can lead to the G0/G1 arrest of the human melanoma A875 cells. In addition, taking the effect exerted by the mogrol on the melanoma A875 cells as an example, details are shown in FIG. 12. It can be seen that with the rise of the concentration of the mogrosides and analogs thereof, the proportion of cells in the G0/G1 phase is gradually increased, and the cell cycle distribution is significantly changed, which indicates that mogrosides and analogs thereof can lead to the G0/G1 arrest of the human melanoma A875 cells, and the cycle arrest effect of the mogrosides and analogs thereof on cancer cells exhibits a dose-dependence, and the results are identical to those of the U937 cells. It indicates that mogrosides and analogs thereof can induce the cell cycle arrest of tumor cells by inhibiting the STAT3 signal pathway and regulating cyclins, so as to inhibit the growth of tumors.

The results obtained after leukemia cell K562 treatment by Mogroside I E1, Mogroside II A2 and mogrol were identical to each other. The cell cycle of the leukemia cells K562 was arrested after the treatment by the mogrosides and analogs thereof. In addition, with the rise of the concentration of the mogrosides and analogs thereof, the proportion of cell arrest is gradually increased, and the cell cycle distribution is significantly changed, which indicates that the mogrosides and analogs thereof can lead to the cell cycle arrest of the leukemia cells K562, and the cycle arrest effect of the mogrosides and analogs thereof on cancer cells exhibits a dose-dependence. It indicates that mogrosides and analogs thereof can induce the cell cycle arrest of tumor cells by inhibiting the STATS signal pathway and regulating cyclins, so as to inhibit the growth of tumors.

Example 6

Figure 13:
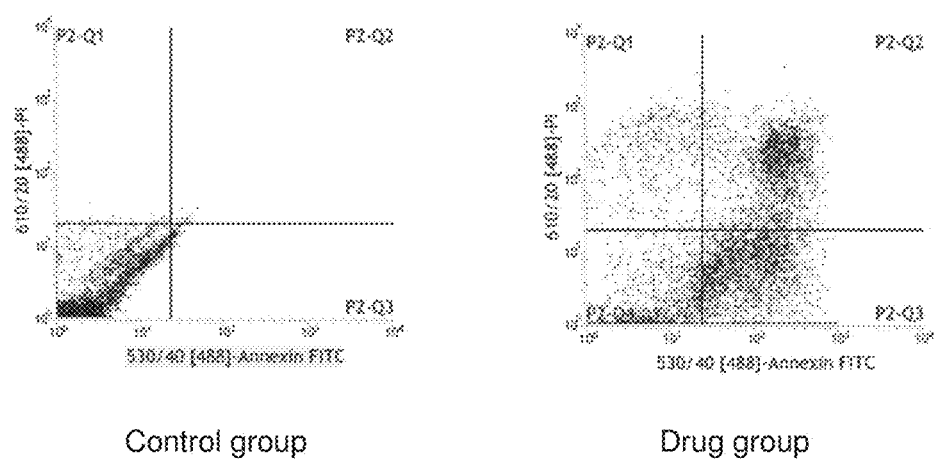
FIG. 13 is a variation diagram of cell apoptosis upon the action of the mogrol on lymphoma U937 cells according to Example 6 of the present invention.
Figure 14:
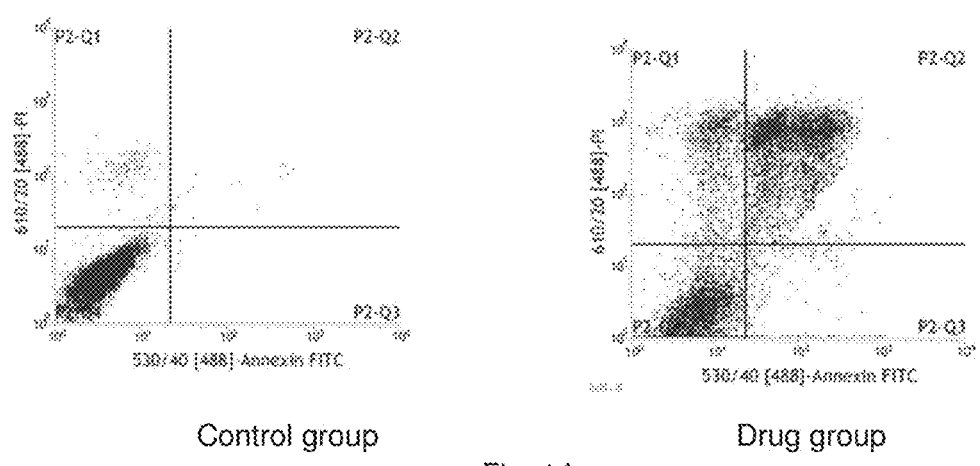
FIG. 14 is a variation diagram of cell apoptosis upon the action of Mogrol I E1 on human melanoma A875 cells according to Example 6 of the present invention.
Figure 15:
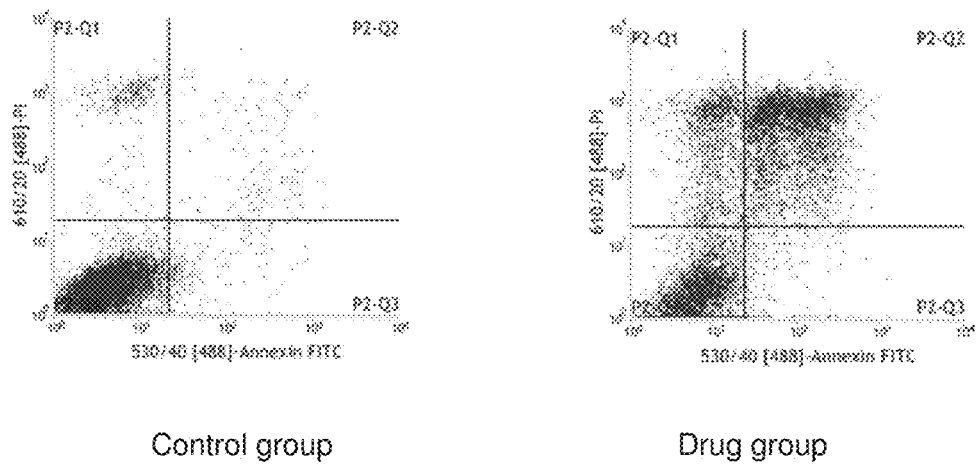
FIG. 15 is a variation diagram of cell apoptosis upon the action of Mogrol II A2 on leukemia cells K562 according to Example 6 of the present invention.

Lymphoma U937 cells, human melanoma A875 cells and leukemia cells K562 in logarithmic growth phase were selected, and after the respective culture with 0 and 10 μmol/L of the mogrosides and analogs thereof (i.e. Mogroside I E1, Mogroside II A2 and mogrol) for 24 h, cells were collected and washed twice with 200 μl of cold PBS, and then the cells were collected again; 100 μl of binding buffer was added for re-suspending the cells, and after the addition of 2 μl of Annexin V-FITC and well mixing, the resulting mixture was placed in dark at room temperature for 10 min, and then 5 μl of propidium iodide (PI) was added and then well mixed; the mixture was placed in dark at room temperature for 10 min, and detected by flow cytometer, and the results are shown in FIGS. 13-15.

The results obtained after U937 cell treatment by Mogroside I E1, Mogroside II A2 and mogrol were identical to each other. Taking the mogrol as an example, the results are shown in FIG. 13. It can be seen that the mogrosides and analogs thereof act on the histiocytic lymphoma U937 cells for 24 h, and mogrol can induce the apoptosis of the histiocytic lymphoma U937 cells. In addition, 0, 10, 150 and 250 μmol/L of the mogrosides and analogs thereof were used for treating the U937 cells for 24 h, and it is concluded that with the rise of the concentration of the mogrosides and analogs thereof, the level of cell apoptosis increases, namely, the effect of the mogrosides and analogs thereof on the lymphoma U937 cells exhibits a dose-dependence.

Figure 16:
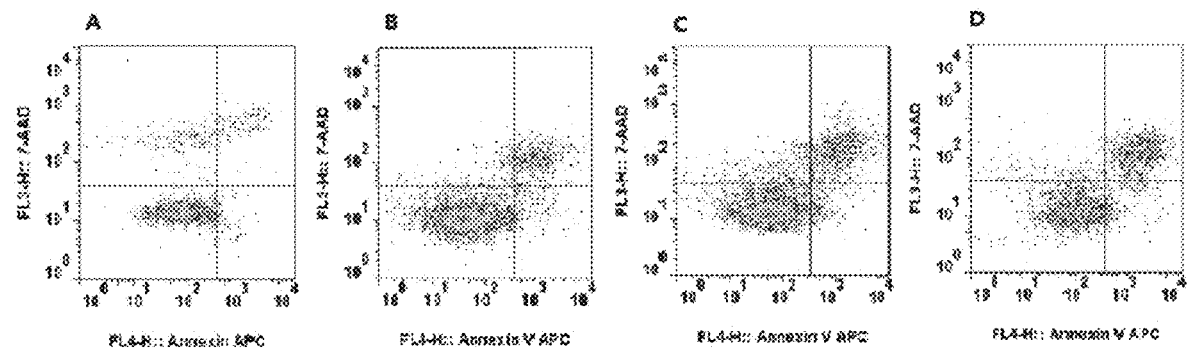
FIG. 16 is a variation diagram of cell apoptosis upon the action of different concentrations of Mogrol II A2 on human melanoma A875 cells according to Example 6 of the present invention.

The results obtained after human melanoma A875 cell treatment by Mogroside I E1 Mogroside II A2 and the mogrol were identical to each other. Taking Mogroside I E1 as an example, the results are shown in FIG. 14. It can be seen that the mogrosides and analogs thereof act on the human melanoma A875 cells for 24 h, and the mogrosides and analogs thereof can induce the apoptosis of the human melanoma A875 cells. Moreover, different concentrations of the mogrosides and analogs thereof were utilized to act on the human melanoma A875 cells. Taking Mogroside II A2 as an example, the results are shown in FIG. 16. It can be seen that with the rise of the concentration of the mogrosides and analogs thereof, the amount for cell apoptosis increases, namely, the effect of the mogrosides and analogs thereof on the human melanoma A875 cells exhibits a dose-dependence. The results are identical to those of the lymphoma U937 cells.

The results obtained after leukemia cell K562 treatment by Mogroside I E1, Mogroside II A2 and the mogrol were identical to each other. Taking Mogroside II A2 as an example, the results are shown in FIG. 15. It can be seen that the mogrosides and analogs thereof act on the leukemia cells K562 for 24 h, and the mogrosides and analogs thereof can induce the apoptosis of the leukemia cells K562. Moreover, different concentrations of the mogrosides and analogs thereof are utilized to act on the leukemia cells K562, and with the rise of the concentration of the mogrosides and analogs thereof, the amount for cell apoptosis increases, namely, the effect of the mogrosides and analogs thereof on the leukemia cells K562 exhibits a dose-dependence. The results are identical to those of the lymphoma U937 cells.

Example 7

Lymphoma U937 cells, human melanoma A875 cells and leukemia cells K562 in logarithmic growth phase were selected, and the concentrations of the cells were adjusted to $1 \times 10^4$ cells/mL, and the cells were transferred to a 6-well plate for culture, and after the 24-hour culture, drugs were added to achieve final concentrations of 0, 10, 100 and 250 μmol/L, wherein only whole medium was added to the negative control groups, while Mogroside II A2 was added to the positive control groups, after 24-hour culture, waste solution was removed, and fixing solution was added to each well for fixing for 25 min, and then the resulting mixture was washed twice, 3 min each time, and then Hoechst 33258 staining solution was added for staining in dark at room temperature for 30 min, and the cell morphology variation was observed using a fluorescence microscope.

Figure 17:
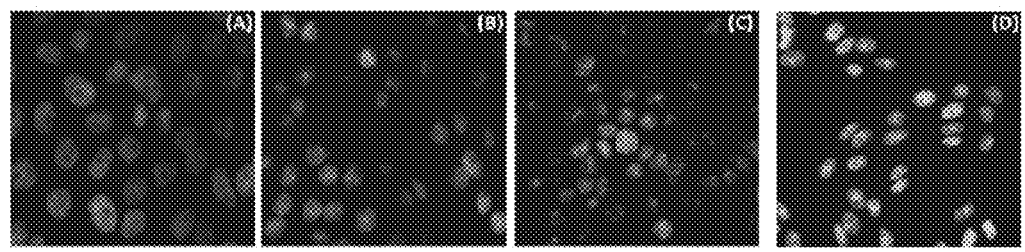
FIG. 17 is a variation diagram of cell morphology observed by fluorescence microscope upon the action of different concentrations of Mogrol II A2 on human melanoma A875 cells according to Example 7 of the present invention.

The view of the A875 melanoma cells under the effect of Mogroside II A2 observed by fluorescence microscope is shown in FIG. 17. In FIG. 17, FIG. A shows a group treated with the culture solution, wherein the cell nucleus under the fluorescence microscope is intact and evenly colored, and the fluorescence is dispersive and relatively dim; and FIGS. B, C, and D show cells of groups treated with 10, 100 and 250 µmol/L respectively, wherein with the increase of the drug concentration, the chromatin thereof exhibits hyperchromatic massive or granular fluorescence, and the cell nucleus chromatin is coagulated, and the cell nucleus undergoes lysis, and the coloring is irregular and exhibits a typical variation of cell apoptosis.

In addition, the action effects of Mogroside II A2 on the lymphoma U937 cells and the leukemia cells K562 are identical to the results of the human melanoma A875 cells. Moreover, the same method was also utilized to respectively treat the human melanoma A875 cells, the lymphoma U937 cells and the leukemia cells K562 with Mogroside I E1 and the mogrol, and the results obtained were identical to the results of Mogroside II A2.

It can be concluded that the mogrosides and analogs thereof can induce the apoptosis of various cancer cells, after that the mogrosides and analogs thereof act on the human melanoma A875 cells, the lymphoma U937 cells and the leukemia cells K562 for 24 h, and the amount for cell apoptosis increased with the rise of the concentration of the mogrosides and analogs thereof, namely, the effect of the mogrosides and analogs thereof on cancer cells exhibits a dose-dependence.

Example 8

Lymphoma U937 cells, human melanoma A875 cells and leukemia cells K562 in logarithmic growth phase were taken, and the cell concentrations were adjusted to $2 \times 10^7$ cells/mL, and then the cells were inoculated to a 96-well culture plate (100 µl each well); and after the pre-culture for 24 h, 100 µl of culture solution prepared in different concentrations were added, such that each group of the mogrosides and analogs thereof had a final concentration of 0.1, 1, 10, 100, 200 and 250 µmol/L (6 doses), respectively, and cells cultured with DMSO were set as control groups.

MTT colorimetric experiments were performed after 24 h, respectively: prior to the finish of each experiment, 15 µl of MTT solution in a concentration of 5 mg/ml was added to each well, and the culture was continued in dark at 37° C. for 4 h, then 150 µl of DMSO was added to each well and oscillating in a shaker for 10 min, and then the residue was placed in a microplate reader to detect the optical density OD) at 490 nm, and the inhibition rate was calculated according to the following formula: cell growth inhibition rate (control group $OD_{490}$—test group $OD_{490}$)/control group $OD_{490} \times 100\%$.

Figure 18:
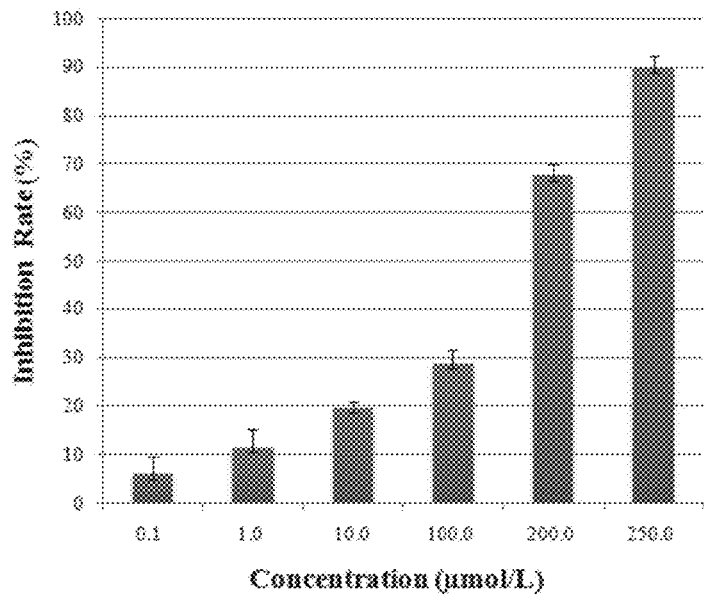
FIG. 18 is a histogram of cell growth inhibition rate upon the action of different concentrations of Mogrol I E1 on lymphoma U937 cells according to Example 8 of the present invention.

The results obtained after U937 cell treatment by Mogrol I E1, Mogrol II A2 and mogrol were identical to each other. Taking Mogrol I E1 as an example, the results are shown in FIG. 18. It can be seen: the MTT experiment results show that the mogrosides and analogs thereof have an inhibitory effect on the proliferation of the histiocytic lymphoma U937 cells, and the inhibition rate thereof increases with the rise of the drug concentration or the prolongation of the action time, and it indicates that the inhibitory effect of the mogrosides and analogs thereof on the proliferation of the histiocytic lymphoma U937 cells has a significant dose-dependence and time-dependence. The ANOVA variance analysis shows that the differences between different dose groups, between different time groups and their differences from the control groups all have a statistical significance.

Figure 19:
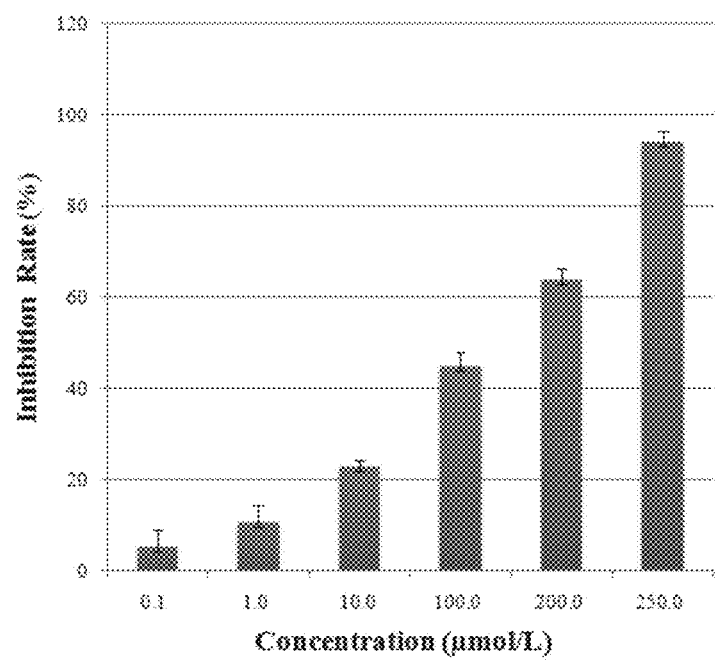
FIG. 19 is a histogram of cell growth inhibition rate upon the action of different concentrations of the mogrol on human melanoma A875 cells according to Example 8 of the present invention.

The results obtained after melanoma A875 cell treatment by Mogrol I E1, Mogrol II A2 and the mogrol were identical to each other. Taking the mogrol as an example, the results are shown in FIG. 19. It can be seen: the MTT experiment results show that mogrosides and analogs thereof have an inhibitory effect on the proliferation of the melanoma A875 cells, and the inhibition rate thereof increases with the rise of the drug concentration or the prolongation of the action time, and it indicates that the inhibitory effect of the mogrosides and analogs thereof on the proliferation of the melanoma A875 cells has a significant dose-dependence and time-dependence. ANOVA variance analysis shows that the differences between different dose groups, between different time groups and their differences from the control groups all have a statistical significance.

Figure 20:
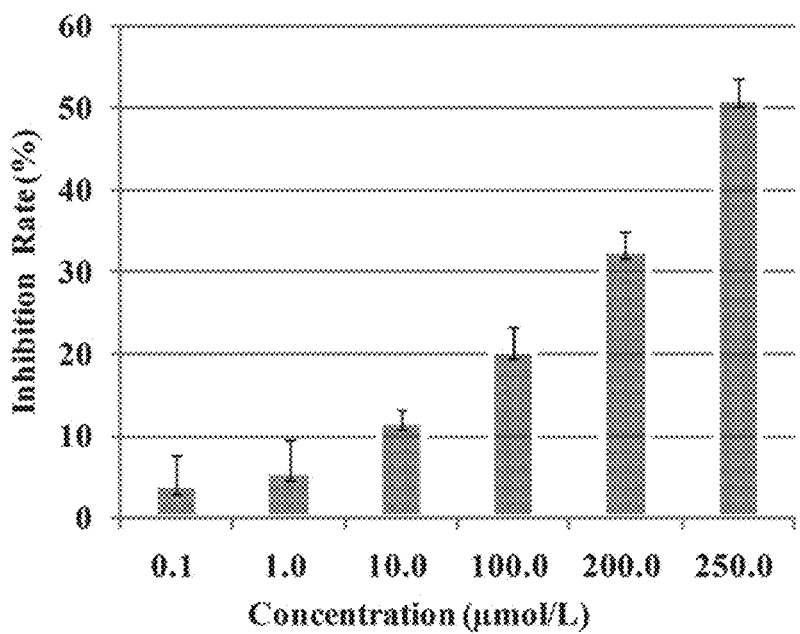
FIG. 20 is a histogram of cell growth inhibition rate upon the action of different concentrations of Mogrol II A2 on leukemia cells K562 according to Example 8 of the present invention.

The results obtained after leukemia cell K562 treatment by Mogrol I E1, Mogrol II A2 and the mogrol were identical to each other. Taking Mogrol II A2 as an example, the results are shown in FIG. 20. It can be seen: the MTT experiment results show that mogrosides and analogs thereof have an inhibitory effect on the proliferation of the leukemia cells K562, and the inhibition rate thereof increases with the rise of the drug concentration or the prolongation of the action time, and it indicates that the inhibitory effect of the mogrosides and analogs thereof on the proliferation of the leukemia cells K562 has a significant dose-dependence and time-dependence. After analysis of variance, the differences between different dose groups, between different time groups and their differences from the control groups all have a significant meaning.

In addition, tests of examples 3 to 8 were also performed regarding prostate cancer cells, renal carcinoma cells, head and neck squamous cell carcinoma cells, lung cancer cells, ovarian cancer cells, breast cancer cells, pancreatic cancer cells, liver cancer cells and colon cancer cells, and the results thereof were all identical to the results of the lymphoma U937 cells.

Moreover, tests of examples 3 to 8 were also performed on Mogrol III, Mogrol IV, Mogroside V and Mogroside VI, and the results thereof were all identical to those of Mogrol I E1 and Mogrol II A2; in addition, tests of examples 3-8 were also performed regarding prostate cancer cells, renal carcinoma cells, head and neck squamous cell carcinoma cells, lung cancer cells, ovarian cancer cells, breast cancer cells, pancreatic cancer cells, liver cancer cells and colon cancer cells, and the results thereof were all identical to the results of the lymphoma U937 cells.

The mogrosides and analogs thereof provided in the present application are prepared into health care products and foodstuffs, e.g. biscuits, chewing gum, beverages, tea, cream candy and dairy products; and they also have a very good inhibitory effect on malignant melanoma, prostate cancer, renal carcinoma, head and neck squamous cell carcinoma, lung cancer, ovarian cancer, breast cancer, pancreatic cancer, liver cancer, colon cancer, lymphoma and leukemia.

The above-mentioned examples explain the STAT3 and ERK signal pathway inhibitor provided in the present invention, which main components, i.e. the mogrosides and analogs thereof, have efficacies of selectively inhibiting the signal pathways of nuclear transcription factors STAT3 and ERK, and of inhibiting tumor cell growth and inducing its apoptosis and inhibiting tumor proliferation. Tumors relating to the STAT3 signal pathway include solid tumors, such as malignant melanoma, prostate cancer, renal carcinoma, head and neck squamous cell carcinoma, lung cancer, ovarian cancer, breast cancer, pancreatic cancer, liver cancer and colon cancer; and non-solid tumors such as lymphoma and leukemia, e.g. large granular lymphocytic leukemia, chronic lymphoblastic leukemia and acute lymphoblastic leukemia. As the mogrosides and analogs thereof have a pharmaceutical value of inhibiting STAT3 and ERK signal pathways, it can be deduced that they also have an inhibitory effect on other cancers relating to STAT3 and ERK signals.

Although the present invention has already been explained and described through specific examples, it shall be aware that many further modifications and variations may also be made without departing from the spirit and scope of the present invention. Thus, it means that all these modifications and variations falling in the scope of the present invention are included in the appended claims.

The invention claimed is:

1. A STAT3 and ERK signal pathway inhibitor, wherein the inhibitor comprises crystalline mogrosides and/or analogs thereof.

2. The STAT3 and ERK signal pathway inhibitor according to claim 1, wherein the crystalline mogrosides and analogs thereof inhibit phosphorylation of a transcription factor STAT3.

3. The STAT3 and ERK signal pathway inhibitor according to claim 1, wherein the crystalline mogrosides and analogs thereof inhibit phosphorylation of ERK.

4. The STAT3 and ERK signal pathway inhibitor according to claim 1, wherein the crystalline mogrosides and analogs thereof comprise mogrosides, salt derivatives of the mogrosides, mogrols and C3- or C24-glycosylated derivatives of the mogrol or salts thereof.

5. The STAT3 and ERK signal pathway inhibitor according to claim 4, wherein the crystalline mogrosides are *Momordica grosvenori* mogrosides.

6. The STAT3 and ERK signal pathway inhibitor according to claim 4, wherein the crystalline mogrosides and analogs thereof are mogrols.

7. A formulation of the STAT3 and ERK signal pathway inhibitor of claim 1, wherein the formulation is selected from an inclusion compound, liposome, microsphere, nanoparticle or emulsion prepared from the crystalline mogroside or analog thereof and pharmaceutically acceptable carriers.

* * * * *